United States Patent [19]

Kitteringham et al.

[11] Patent Number: 4,569,996

[45] Date of Patent: Feb. 11, 1986

[54] PROCESS FOR PREPARING SUBSTITUTED PYRIMIDINONES

[75] Inventors: John Kitteringham, Hertford; Brian P. Slingsby, St. Albans, both of England

[73] Assignee: Smith Kline & French Laboratories Limited, Welwyn Garden City, England

[21] Appl. No.: 517,543

[22] Filed: Jul. 27, 1983

[30] Foreign Application Priority Data

Jul. 30, 1982 [GB] United Kingdom ............... 8222096

[51] Int. Cl.$^4$ ........................................... C07D 239/02
[52] U.S. Cl. .................... 544/320; 544/321; 546/276; 548/134; 548/138; 548/190; 548/214; 549/472; 549/75
[58] Field of Search ............................... 544/320, 321

[56] References Cited

U.S. PATENT DOCUMENTS

| | | | |
|---|---|---|---|
| 4,128,658 | 12/1978 | Price et al. | 424/285 |
| 4,154,834 | 5/1979 | Brown et al. | 424/251 |
| 4,165,378 | 8/1979 | Gilman et al. | 424/270 |
| 4,218,452 | 8/1980 | Brown et al. | 424/251 |
| 4,234,588 | 11/1980 | Brown et al. | 424/251 |
| 4,255,428 | 3/1981 | Brown et al. | 544/320 |
| 4,293,557 | 10/1981 | Shibata et al. | 424/267 |
| 4,352,933 | 10/1982 | Lam | 544/320 |
| 4,385,058 | 5/1983 | Cooper et al. | 424/251 |

FOREIGN PATENT DOCUMENTS

| | | | |
|---|---|---|---|
| 24873 | 8/1979 | European Pat. Off. | 544/320 |
| 17680 | 10/1980 | European Pat. Off. | |
| 49173 | 4/1982 | European Pat. Off. | |
| 2546510 | 4/1976 | Fed. Rep. of Germany | |

OTHER PUBLICATIONS

Derwent Abstract 38240C(WP8000966).
Perrin, Dissociation Constants of Organic Bases in Aqueous Solution, (1965), pp. 213, 222.
Peter Sykes, A Guidebook to Mechanism in Organic Chemistry, (1961), p. 154.
Yoneda et al., *Heterocycles*, 12:691–694, (1979).

*Primary Examiner*—Donald G. Daus
*Assistant Examiner*—Cecilia Shen
*Attorney, Agent, or Firm*—Joan S. Keps; Richard D. Foggio; Alan D. Lourie

[57] ABSTRACT

This invention provides a process for the preparation of pyrimidinone compounds with a group $R^2CH(OH)$— at the 5-position thereof, wherein $R^2$ is an optionally substituted acid-stable 5- or 6-membered nitrogen-containing heteroaryl group. The pyrimidinone ring is further substituted by a side-chain of a $H_1$-antagonist or $H_2$-antagonist or a precursor thereof.

The compounds are convertible to 5-heteroaryl methyl compounds which are either useful $H_1$- or $H_2$-antagonists or precursors thereof.

4 Claims, No Drawings

PROCESS FOR PREPARING SUBSTITUTED PYRIMIDINONES

The present invention relates to a process for the preparation of pyrimidones which are useful intermediates in the synthesis of compounds having activity as histamine antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427(1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine $H_1$- and $H_2$-receptors and blockade of both types of receptors is useful. These conditions include inflammation mediated by histamine, for example skin inflammation, and those hypersensitivity responses due to the action of histamine at $H_1$- and $H_2$-receptors, for example allergies.

Accordingly the present invention provides a process for the preparation of a compound of the formula (I):

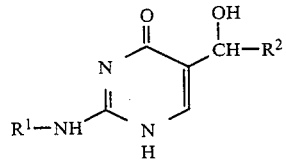

wherein $R^1$ is:
hydrogen, a group $QCH_2CH_2—$ or $QCH_2CH_2CH_2—$ wherein Q is mercapto or a protected derivative thereof, or $R^1$ is a group $R^3—X—Y—(CH_2)_n—$
wherein $R^3$ is:
2- or 4-imidazolyl optionally substituted by $C_{1-4}$alkyl, halo, trifluoromethyl or hydroxymethyl;
2-pyridyl optionally substituted in the 4-position by a group $—CH_2NR^4R^5$, or optionally substituted by one or more $C_{1-4}$alkyl, $C_{1-4}$alkoxy, halo, amino or hydroxy moieties;
2-thiazolyl;
3-isothiazolyl optionally substituted by chloro or bromo;
3-(1,2,5)-thiadiazolyl optionally substituted by chloro or bromo;
2-(5-amino)-(1,3,4)-thiadiazolyl;
2-guanidino-4-thiazolyl;
2-furanyl substituted in the 5-position by a group $—(CH_2)_mNR^4R^5$; or 2-thienyl optionally substituted in the 5-position by a group $—(CH_2)_mNR^4R^5$; or optionally substituted phenyl;
wherein $R^4$ and $R^5$ are independently $C_{1-4}$alkyl or $R^4$ and $R^5$ together with the nitrogen atom to which they are attached form a pyrrolidino or piperidino ring; and m is 1 to 4;
n is 2; or if $R^3$ is furanyl or optionally substituted thienyl as hereinbefore defined then n may also be 3;
Y is oxygen, sulphur or methylene;
X is methylene, or if Y is methylene and $R^3$ is optionally substituted phenyl or pyridyl then X may also be oxygen;
and $R^2$ is an optionally substituted acid-stable, 5- or 6-membered nitrogen-containing heteroaryl group:
which process comprises the reaction of a compound of the formula (II):

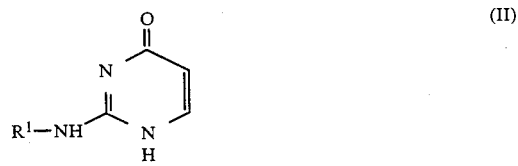

wherein $R^1$ is as defined in relation to formula (I), with a compound of the formula (III):

wherein $R^2$ is as defined in relation to formula (I), in the presence of an acid.

In general one equivalent or an excess of the compound of the formula (III) is used in this process. For example about 1 to 4 mole equivalents of the compound of the formula (III) may be used.

Suitably the process is performed in an acidic solvent in which the compounds of the formulae (II) and (III) are substantially soluble. Suitable acids include organic acids such as acetic acid, and inorganic mineral acids for example polyphosphoric acid, phosphoric acid, sulphuric acid, hydrobromic acid, hydroiodic acid and hydrochloric acid. Preferably any such acid should be concentrated. A particularly useful solvent is concentrated hydrochloric acid.

The process is generally conducted at an ambient or an elevated temperature; we have found it particularly convenient to perform the reaction at reflux temperature.

The desired compound of the formula (I) may be isolated from the reaction mixture in conventional manner, for example the reaction mixture may be treated with a base such as sodium hydroxide, and the product tends to separate as an oil. This oil, if desired, may be purified by chromatography and/or crystallisation.

It is surprising that the reaction sequence of the present invention is successful as it has been found that aryl-bis(pyrimidin-5-yl)methanes are by-products when a 2,4-disubstituted pyrimidine is condensed with benzaldehyde or with benzaldehydes substituted with any substituent which is not of a high electronegative nature. Also certain heterocyclic aldehydes such as thienylaldehyde or furfuraldehyde either do not react with the 2,4-disubstituted pyrimidine, decompose or give bis compounds.

Suitably in the compounds of the formula (II) for use in this process $R^1$ is a group $R^3—X—Y—(CH_2)_n—$ as hereinbefore defined.

Suitably X is methylene.
Suitably Y is sulphur or methylene.
Suitably n is 2.

Thus in a preferred aspect $R^3—X—Y—(CH_2)_n—$ represents $R^3CH_2SCH_2CH_2—$. Thus in another preferred aspect $R^3—X—Y—(CH_2)_n—$ represents $R^3(CH_2)_4—$.

Suitably $R^3$ is 4-imidazolyl optionally substituted in the 5-position by methyl or bromo; or 2-guanidino-4-thiazolyl.

Suitably $R^3$ is 2-pyridyl, substituted in the 4-position by dimethylaminomethyl, piperidinomethyl or pyrrolidinomethyl.

Suitably also $R^3$ is 2-furanyl substituted in the 5-position by dimethylaminomethyl, piperidinomethyl or pyrrolidinomethyl. Suitably also $R^3$ is 2-thienyl substituted in the 5-position by dimethylaminomethyl, piperidinomethyl or pyrrolidinomethyl.

More suitably, and in particular when $—X—Y(CH_2)_n—$ represents $—(CH_2)_4—$, $R^3$ is 2-pyridyl substituted in the 3-position by $C_{1-4}$alkyl such as methyl, $C_{1-4}$alkoxy such as methoxy, halo such as chloro, or amino, or further optionally substituted in the 5-position by halo or $C_{1-4}$alkyl.

When $R^3$ is optionally substituted phenyl suitably it is of the sub-formula (i):

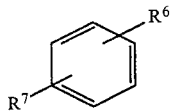

wherein $R^6$ is hydrogen, $C_{1-4}$alkyl, $C_{1-4}$alkoxy, hydroxy, halo, trifluoromethyl, nitro, amino, $C_{1-4}$alkylamino, or di-$(C_{1-4})$alkylamino; and $R^7$ is in the 3-, 4- or 5-position and is hydrogen, amino($C_{1-4}$)alkyl, $C_{1-4}$alkylamino($C_{1-4}$)alkyl, di-$(C_{1-4})$alkylamino($C_{1-4}$)alkyl, piperidino($C_{1-4}$)alkyl, pyrrolidino($C_{1-4}$)alkyl, or $R^7$ is ethoxy or propoxy either of which are ω-substituted by amino, $C_{1-4}$alkylamino, di-$(C_{1-4})$alkylamino, piperidino or pyrrolidino.

In a further aspect $R^1$ is a group $QCH_2CH_2—$ or $QCH_2CH_2CH_2$ wherein Q is mercapto (—SH) or a protected derivative thereof. Any such protected derivative should be one that is convertible to the mercapto compound, or itself is useful, in the subsequent preparation of compounds of the formula (I) wherein $R^1$ is a group $R^3—CH_2—S—(CH_2)_n—$. For example the protection may be in the form of a disulphide.

In a further aspect the process of this invention may be performed on a protected derivative of a compound of the formula (II), which protecting group (or groups) may be converted to the desired substituent(s) to form a compound of the formula (I) as hereinbefore defined. Alternatively the compound of the formula (I) in protected form may be taken through to form a compound of the formula (IV) in protected form, whereupon the protecting group or groups are removed. Such protecting groups are those known in the art to the skilled man as being suitable under the conditions of the process of this invention, and include substituents such as nitro which may be converted to amino.

In the compound of the formula (III) for use in the process of this invention, $R^2$ may in addition to one nitrogen atom optionally contain one or two atoms selected from nitrogen, oxygen or sulphur.

Suitably $R^2$ is a 2-pyridyl, 3-pyridyl, 4-pyridyl, 2-thiazolyl, 2-oxazolyl, 2-imidazolyl, 2-pyrimidyl or 2-pyrazyl ring.

Preferably $R^2$ is a 3-pyridyl or 4-pyridyl ring.

Suitable optional substituents for $R^2$ include $C_{1-4}$alkyl for example methyl or ethyl, $C_{1-4}$alkoxy for example methoxy or ethoxy, or hydroxy. It should be realised that under the reaction conditions compounds of the formula (III) wherein $R^2$ is substituted by $C_{1-4}$alkoxy tend to yield compounds of the formula (I) wherein $R^2$ is substituted by hydroxy.

It is particularly preferred that $R^2$ is 6-methyl-3-pyridyl.

The compounds of the formula (I) are novel and as such form part of the present invention. A chiral centre is present at the carbon atom adjacent to $R^2$, and this invention encompasses both enantiomers.

The compounds of the formula (I) may be converted to histamine antagonists of the formula (IV):

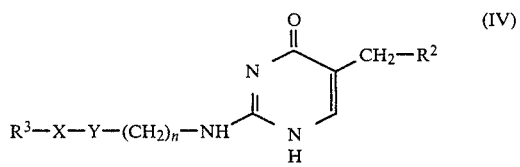

or a pharmaceutically acceptable acid addition salt thereof, wherein $R^3$, X, Y, n and $R^2$ are as hereinbefore defined by carrying out one or more of the following processes:

(i) reducing $R^2CH(OH)—$ to $R^2CH_2—$;

(ii) if necessary removing the mercapto protecting group and reacting with $R^3CH_2L$ wherein L is a group displaceable by mercaptan;

(iii) wherein $R^1$ is hydrogen, reacting with $R^3—X—Y—(CH_2)_n—Q^1$ wherein $Q^1$ is a group displaceable by amine;

(iv) wherein $R^1$ is hydrogen and it is desired to make a compound wherein $R^1$ is $R^3—CH_2S(CH_2)_n—$ then reacting with $HSCH_2CH_2Q^1$ and subsequently with $R^3CH_2L$ wherein L is a group displaceable by mercaptan;

(v) if desired forming a pharmaceutically acceptable acid addition salt.

The steps (i) to (v) described hereinabove may be performed in any convenient and reasonable order.

$R^2CH(OH)—$ may be reduced to $R^2CH_2—$ in conventional manner. Such reduction should of course be carried out under conditions to which the remainder of the molecule is stable, for example using triethylamine-formic acid, zinc-acetic acid, or hydriodic acid-acetic anhydride-acetic acid. Alternatively catalytic hydrogenation may be performed for example using a transition metal catalyst, preferably a Palladium catalyst such as Palladium on Carbon. The hydrogenation reaction may be performed at atmospheric or an elevated pressure, for example between 1–6 atmospheres. The hydrogenation reaction is preferably performed in an acidic medium, for example acetic acid.

In a preferred aspect the reduction is performed with hydriodic acid-acetic anhydride-acetic acid, as this reagent may also be used for the conversion of a compound of the formula (II) to a compound of the formula (I). Thus there is no need to isolate the intermediate of the formula (I).

The acid stable nitrogen protecting group and the mercapto protecting group may be removed in conventional manner.

Examples of a group $Q^1$, displaceable by amine, are halo such as chloro, and acyloxy such as acetyloxy. Such a displacement reaction (steps iii and iv above) is preferably performed in the presence of a solvent, for example a $C_{1-6}$alkanol, at an elevated temperature for example at the reflux temperature of the solvent.

Examples of a group L, displaceable by mercaptan, are chloro, bromo, hydroxy, $C_{1-6}$alkanoyloxy such as acetoxy, arylsulphonyloxy such as 4-methylbenzenesulphonyloxy, $C_{1-6}$alkylsulphonyloxy such as methanesulphonyloxy and triarylphosphonium such as triphenylphosphonium. Preferably L is hydroxy and the reaction (step iv above) is carried out under acidic conditions. When L is chloro or bromo the reaction is preferably performed in the presence of a strong base, for example with sodium ethoxide in ethanol. When L is triarylphosphonium the reaction is preferably carried out under neutral conditions, for example in a halogenated hydrocarbon for example chloroform. When L is aryl- or alkyl-sulphonyloxy the reaction is preferably carried out under mildly basic conditions, for example in pyridine solution.

The starting-materials for the process of this invention, that is the compounds of the formula (II), are either known or may be prepared in an analogous manner to methods known for the preparation of pyrimidone containing histamine-antagonists, for example the compounds of the formula (II) wherein $R^1$ is not hydrogen may be prepared by the reaction of a compound of the formula (V):

wherein $Q^2$ is a group displaceable by amino with a compound of the formula (VI) or (VII):

$$R^3-X-Y-(CH_2)_n-NH_2 \quad (VI)$$

$$Q-(CH_2)_n-NH_2 \quad (VII)$$

wherein $R^3$, X, Y, n and Q are as defined in relation to formula (I). Examples of groups $Q^2$ include nitroamino, $C_{1-6}$alkylthio, benzylthio, chloro or bromo. The process may be carried out in the absence of a solvent at an elevated temperature or in the presence of a non-reactive polar solvent. For example when $Q^2$ is nitroamino the reaction can be carried out in a $C_{1-6}$-alkanol such as ethanol or 2-propanol, pyridine or anisole at the reflux temperature of the reaction mixture, or when $Q^2$ is methylthio the reaction can be carried out in the absence of solvent at 140°–170° C. or in refluxing pyridine.

The following Examples illustrate this invention and its use.

EXAMPLE 1

2-[[4-(3-Methoxy-2-pyridyl)butyl]amino]-5-[(4-pyridyl)hydroxymethyl]-4-(1H)-pyrimidinone 2-[[4-(3-Methoxy-2-pyridyl)butyl]amino]-4-(1H)-pyrimidinone (0.14 g) and pyridine-4-aldehyde (0.06 g) were refluxed in concentrated hydrochloric acid (1 ml) for 5 hours. The solution was cooled and neutralised by the addition of potassium bicarbonate. Water (2 ml) was added, the aqueous layer was then decanted from the red coloured oil which was washed with more water. The oil was subjected to chromatography on silica gel using gradient elution (100% chloroform→2% Methanol in chloroform). The fractions containing the desired product were collected, combined and evaporated under reduced pressure to afford the title compound as an oil; $\delta(CDCl_3)$ 1.67 (4H, m), 2.80 (2H, t), 3.36 (2H, m), 3.80 (3H, s), 5.72 (1H, s), 7.07 (2H, d), 7.35 (2H, d), 7.49 (1H, s), 7.87 (1H, t), 8.43 (2H, m) ppm.

EXAMPLE 2

2-[[4-(3-Chloro-2-pyridyl)butyl]amino]-5-[(4-pyridyl)-hydroxymethyl]-4-(1H)-pyrimidinone 2-[[4-(3-Chloro-2-pyridyl)butyl]amino]-4-(1H)-pyrimidinone (1.37 g) and pyridine 4-aldehyde (0.52 g) were refluxed in concentrated hydrochloric acid (5 ml) for 24 hours. The reaction mixture was evaporated under reduced pressure to afford an oil which was partitioned between chloroform (25 ml) and water (25 ml) with the addition of sodium hydroxide to take the aqueous layer to pH 6.5. The aqueous layer was washed with more chloroform (25 ml) and the combined chloroform extracts were dried (MgSO₄) and evaporated under reduced pressure to give a red oil (1.5 g). This oil was stirred under hot diethyl ether which was subsequently decanted (removing some pyridine-4-aldehyde), and the oil was subjected to chromatography on silica gel with gradient elution (100% chloroform→5% methanol in chloroform). The fractions containing the desired product were collected, combined and evaporated under reduced pressure to an oil which solidified on trituration with diethyl ether. Crystallisation from aqueous ethanol afforded a white crystalline solid (0.78 g). This was further purified by dissolution in chloroform, washing with sodium hydroxide solution (pH 13), extraction into dilute hydrochloric acid (pH 4), washing with chloroform, taking to pH 7.5 and extracting back into chloroform. This was evaporated under reduced pressure to afford an oil which was crystallised from aqueous ethanol to afford the title compound (0.53 g), m.p. 90° C.; $\delta(CDCl_3)$ 1.75 (4H, m), 2.95 (2H, m), 3.40 (2H, m), 5.71 (1H, s), 7.07 (1H, dd), 7.32 (2H, d), 7.40 (3H, br), 7.46 (1H, s), 7.62 (1H, dd), 8.23 (1H, dd), 8.49 (2H, d) ppm.

EXAMPLE 3

2-[[4-(3-Methoxy-2-pyridyl)butyl]amino]-5-[(6-methyl-3-pyridyl)hydroxymethyl]-4-(1H)-pyrimidinone 2-[[4-(3-Methoxy-2-pyridyl)butyl]amino]-4-(1H)-pyrimidinone (1.42 g, 0.005 mol) was dissolved in concentrated hydrochloric acid (10 ml) and 2-methyl-5-formylpyridine (1.35 g, 0.012 mol) was added. The solution was stirred at reflux temperature for 24 hours, cooled, basified with 10N sodium hydroxide to pH 8.5 and the product left to separate as an oil. The aqueous mother liquor was decanted and the oil subjected to medium pressure liquid chromatography (Kieselgel 60, 230–400 mesh) with methanolic ammonia: dichloromethane (10:90) as eluent. The relevant fractions were combined and evaporated under reduced pressure to afford the title compound (0.63 g). Crystallisation from aqueous methanol afforded the title product as a white crystalline solid, m.p. 82° C.; δ(CDCl₃) 1.6 (4H, m), 2.5 (3H, s) 2.75 (2H, m), 3.3 (2H, m), 3.8 (3H, s), 5.7 (1H, s), 7.1 (3H, m), 7.4 (1H, s), 7.65 (1H dd), 7.9 (1H, dd), 8.5 (1H, m) ppm.

EXAMPLE 4

2-[[4-(3-Methoxy-2-pyridyl)butyl]amino]-5-[(6-methyl-3-pyridyl)methyl]-4-(1H)-pyrimidinone 2-[[4-(3-Methoxy-2-pyridyl)butyl]amino]-5-[(6-methyl-3-pyridyl)hydroxymethyl]-4-(1H)-pyrimidinone (0.99 g, 0.0025 mol), triethylamine (0.57 g, 0.0055 mol) and 98% formic acid (0.75 g, 0.015 mol) were stirred at reflux temperature for 4½ hours. The reaction mixture was cooled, diluted with water (3 ml) and basified with ammonia solution (specific gravity 0.880) to pH 8.5. The aqueous solution was extracted into dichloromethane (2×5 ml); the organic layers were combined, dried over sodium carbonate, filtered and evaporated under reduced pressure to afford a foam. This foam was subjected to medium pressure liquid chromatography (Kieselgel 60, 230–400 Mesh) with methanolic ammonia: dichloromethane (10: 90). The relevant fractions were combined and evaporated under reduced pressure to afford the title compound (0.40 g). Crystallisation form ethanolic HCl afforded 2-[[4-(3-methoxy-2-pyridyl)butyl]amino]-5-[(6-methyl-3-pyridyl)methyl]-4-(1H)-pyrimidinone trihydrochloride as a crystalline solid m.p. 213° C.; nmr of the free base δ(CDCl₃) 1.7 (4H, m), 2.5 (3H, s), 2.75 (2H, m), 3.3 (2H, m), 3.6 (2H, s), 3.8 (3H, s), 7.1 (3H, m), 7.4 (1H, s), 7.45 (1H, dd), 8.0 (1H, dd), 8.4 (1H, dd) ppm.

EXAMPLE 5

2-Methyl-5-formylpyridine is reacted with:
(a) 2-(2-(5-methyl-4-imidazolylmethylthio)ethylamino)-4(1H)-pyrimidinone
(b) 2-(2-(2-thiazolylmethylthio)ethylamino)-4(1H)-pyrimidinone
(c) 2-(2-(2-guanidino-4-thiazolylmethylthio)ethylamino)-4(1H)-pyrimidinone
(d) 2-(2-(3-isothiazolylmethylthio)ethylamino)-4(1H)-pyrimidinone
(e) 2-(2-(5-dimethylaminomethyl-2-furanylmethylthio)ethylamino)-4(1H)-pyrimidinone
(f) 2-(2-(5-dimethylaminomethyl-2-thienylmethylthio)ethylamino)-4(1H)-pyrimidinone
(g) 2-(3-(4-dimethylaminomethyl-2-pyridyloxy)-propylamino)-4(1H)-pyrimidinone
(h) 2-(3-(4-piperidinomethyl-2-pyridyloxy)-propylamino)-4(1H)-pyrimidinone
(i) 2-(2-(3-dimethylaminomethylphenylmethylthio)ethylamino)-4(1H)-pyrimidinone in refluxing concentrated hydrochloric acid for 24 hours to give:
(a) 2-(2-(5-methyl-4-imidazolylmethylthio)ethylamino-5-((6-methyl-3-pyridyl)hydroxymethyl)-4(1H)-pyrimidinone
(b) 2-(2-(2-thiazolylmethylthio)ethylamino)-5-((6-methyl-3-pyridyl)hydroxymethyl)-4(1H)-pyrimidinone
(c) 2-(2-(2-guanidino-4-thiazolylmethylthio)ethylamino)-5-((6-methyl-3-pyridyl)hydroxymethyl)-4(1H)-pyrimidinone
(d) 2-(2-(3-isothiazolylmethylthio)ethylamino)-5-((6-methyl-3-pyridyl)hydroxymethyl)-4(1H)-pyrimidinone
(e) 2-(2-(5-dimethylaminomethyl-2-furanylmethylthio)ethylamino)-5-((6-methyl-3-pyridyl)hydroxymethyl)-4(1H)-pyrimidinone
(f) 2-(2-(5-dimethylaminomethyl-2-thienylmethylthio)ethylamino)-5-((6-methyl-3-pyridyl)hydroxymethyl)-4(1H)-pyrimidinone
(g) 2-(3-(4-dimethylaminomethyl-2-pyridyloxy)-propylamino)-5-((6-methyl-3-pyridyl)hydroxymethyl)-4(1H)-pyrimidinone
(h) 2-(3-(4-piperidinomethylaminomethyl-2-pyridyloxy)propylamino)-5-((6-methyl-3-pyridyl)hydroxymethyl)-4(1H)-pyrimidinone
(i) 2-(2-(3-dimethylaminomethylphenylmethylthio)ethylamino)-5-((6-methyl-3-pyridyl)hydroxymethyl)-4(1H)-pyrimidinone

EXAMPLE 6

2-Formylpyridine is reacted with 2-(4-(3-methoxy-2-pyridyl)butylamino)-4(1H)-pyrimidinone in refluxing concentrated hydrochloric acid for 24 hours to give 2-(4-(3-methoxy-2-pyridyl)butylamino)-5-((2-pyridyl)hydroxymethyl)-4(1H)-pyrimidinone.

EXAMPLE 7

4-Formyl-2-methoxypyridine is reacted with 2-(2-(5-dimethylaminomethyl-2-furanylmethylthio)ethylamino)-4(1H)-pyrimidinone in refluxing concentrated hydrochloric acid for 24 hours to give 2-(2-(3-dimethylaminomethylfuranylmethylthio)ethylamino)-5-((2-hydroxy-4-pyridyl)hydroxymethyl)-4(1H)-pyrimidinone.

EXAMPLE 8

Isocytosine is reacted with 2-methyl-5-formyl pyridine in refluxing concentrated hydrochloric acid for 24 hours to give 2-amino-5-((6-methyl-3-pyridyl)hydroxymethyl)-4(1H)-pyrimidinone.

EXAMPLE 9

Bis-[2-((4(1H)-pyrimidin-2-one)amino)ethyl]disulphide is reacted with 2-methyl-5-formyl pyridine in refluxing concentrated hydrochloric acid for 24 hours to give bis-[2-((4(1H)-(5-(6-methyl-3-pyridyl)hydroxymethyl)pyrimidin-2-one)amino)ethyl]disulphide.

What is claimed is:

1. A process for the preparation of a compound of the formula (I):

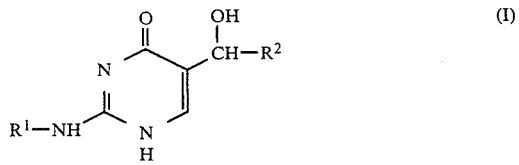

wherein R¹ is:
hydrogen, a group QCH₂CH₂— or QCH₂CH₂CH₂— wherein Q is mercapto, or R¹ is a group R³—X—Y—(CH₂)ₙ—
wherein R³ is:

2- or 4-imidazolyl optionally substituted by one $C_{1-4}$alkyl, halo, trifluoromethyl or hydroxymethyl;

2-pyridyl optionally substituted in the 4-position by a group —$CH_2NR^4R^5$, or optionally substituted by one or two $C_{1-4}$alkyl, $C_{1-4}$alkoxy, halo, amino or hydroxy moieties;

2-thiazolyl;

3-isothiazolyl optionally substituted by one chloro bromo;

3-(1,2,5)-thiadiazolyl optionally substituted by one chloro or bromo;

2-(5-amino)-(1,3,5)-thiadiazolyl;

2-guanidino-4-thiazolyl;

2-furanyl substituted in the 5-position by a group —$(CH_2)_mNR^4R^5$ or 2-thienyl optionally substituted in the 5-position by a group —$(CH_2)_mNR^4R^5$;

or phenyl of the sub-formula (i):

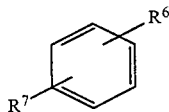
(i)

wherein $R^6$ is hydrogen, $C_{1-4}$alkyl, $C_{1-4}$alkoxy, hydroxy, halo, trifluoromethyl, nitro, amino, $C_{1-4}$alkylamino, or di-$(C_{1-4})$alkylamino; and $R^7$ is in the 3-, 4- or 5-position and is hydrogen, amino($C_{1-4}$) alkyl, $C_{1-4}$alkylamino($C_{1-4}$)alkyl, di-$(C_{1-4})$alkylamino-$(C_{1-4})$alkyl, piperidino$(C_{1-4})$alkyl, pyrrolidino-$(C_{1-4})$alkyl, or $R^7$ is ethoxy or propoxy either of which are ω-substituted by amino, $C_{1-4}$alkylamino, di-$(C_{1-4})$alkylamino, piperidino or pyrrolidino;

wherein $R^4$ and $R^5$ are independently $C_{1-4}$alkyl or $R^4$ and $R^5$ together with the nitrogen atom to which they are attached form a pyrrolidino or piperidino ring; and m is 1 to 4;

n is 2; or if $R^3$ is substituted furanyl or optionally substituted theinyl as hereinbefore defined then n may also be 3;

Y is oxygen, sulphur or methylene;

X is methylene, or if Y is methylene and $R^3$ is phenyl of the sub-formula (i) or optionally substituted pyridyl then X may also be oxygen;

and $R^2$ is an optionally mono-substituted acid-stable, 5- or 6-membered nitrogen-containing heteroaryl group wherein the heteroaryl group is pyridyl, thiazolyl, oxazolyl, imidazolyl, pyrimidyl or pyrazyl; and optional substituents are $C_{1-4}$alkyl, $C_{1-4}$alkoxy and hydroxy:

which process comprises the reaction of a compound of the formula (II):

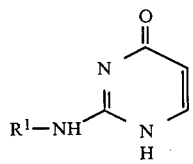
(II)

wherein $R^1$ is as defined in relation to formula (I), with a compound of the formula (III):

$R^2$—CHO (III)

wherein $R^2$ is as defined in relation to formula (I), in the presence of an acid.

2. A process according to claim 1 performed in the acidic solvent.

3. A process according to claim 2 wherein the solvent is concentrated hydrochloric acid.

4. A process according to claim 2 wherein the solvent is hydriodic acid.